United States Patent [19]

Winkelmann et al.

[11] Patent Number: 5,580,596
[45] Date of Patent: Dec. 3, 1996

[54] SPROUT INHIBITOR FOR POTATOES

[75] Inventors: H. H. Winkelmann, Munich; Gottfried Robl, Grasbrunn; Diethart Henning, Schinne, all of Germany

[73] Assignee: CPC International Inc., Englewood Cliffs, N.J.

[21] Appl. No.: 253,639

[22] Filed: Jun. 3, 1994

[30] Foreign Application Priority Data

Jun. 4, 1993 [DE] Germany ..................... 43 18 673.4

[51] Int. Cl.$^6$ ....................................... A23L 3/34
[52] U.S. Cl. ..................... 426/321; 426/637; 504/118
[58] Field of Search ..................... 426/321, 637; 504/118

[56] References Cited

U.S. PATENT DOCUMENTS

| | | | |
|---|---|---|---|
| 5,129,951 | 7/1992 | Vaughn et al. ............... | 504/118 X |
| 5,139,562 | 8/1992 | Vaughn et al. ............... | 504/118 X |

FOREIGN PATENT DOCUMENTS

| | | |
|---|---|---|
| 0287946 | 10/1988 | European Pat. Off. . |
| 146237 | 9/1979 | Germany . |
| 209378 | 8/1982 | Germany . |
| 9309212 | 5/1993 | WIPO . |

OTHER PUBLICATIONS

Patent Abstracts of Japan, JPA, 03 197 402 (Dai Ichi Seiyaku Co Ltd) Aug. 28, 1991.
Patent Abstracts of Japan, JP,A,57 014 504 (Res. Inst. for Prod Dev) Jan. 25, 1982.
Chemistry & Industry, No. 3, Feb. 4, 1985, "Review of Current Usage of Pesticide Chemicals for the Control of Post–Harvest Losses in Stored Potatoes" Author: Tim J. Dent, pp. 84–87.

Primary Examiner—Leslie Wong

[57] ABSTRACT

The invention relates to a sprout inhibitor for potatoes which, as the main component, contains rape oil methylester and/or specific long-chain alcohols, eventually in mixture with the medium- and/or long-chain alcohols known for said purpose, and/or ethereal oil and/or the known chemical sprout-inhibitor agents, or to the use of rape oil methylester alone or the use of $C_{18}$ to >$C_{36}$-alcohols such as Espum EGA 162 (now Dehysan) alone, or in a mixture with rape oil methylester and/or other known sprout-inhibiting agents.

11 Claims, No Drawings

SPROUT INHIBITOR FOR POTATOES

The invention relates to a sprout inhibitor for potatoes, which substantially consists of rape oil methylester, medium- or long-chain alcohols or combinations thereof, or a composition based on rape oil methylester, medium- or long-chain alcohols or combinations thereof.

The potatoes harvested in the fall are frequently expected to be stored through the winter and far into the coming spring at least until early potatoes are available again.

Even with the cool storage of potatoes, as is usually done in the potato-processing industry, the potatoes start to sprout even after a few weeks when stored at 6° to 8° C., and are considerably sprouted after three to four months.

The use of sprout-inhibiting agents has been known for a long time. Known sprout inhibitors are certain ethereal oils, in particular peppermints, and also those of the "muna" plant, which is related to peppermint. Peppermint oils and "muna" oils are relatively expensive, so that any industrial application based only on said ethereal oils is not feasible.

The chemical agents recently used for sprout inhibition in connection with potatoes include propham, i.e. isopropylphenyl carbamate, alone or in combination with chloropropham; however, the compound has a herbicidal effect, so that its use is not absolutely safe.

Also known are medium-chain and long-chain alcohols, in particular $C_{17}$-$C_{24}$-alcohols which are collected in industry. Said alcohols are frequently combined with propham and/or chloropropham when used as sprout inhibitors.

Reference is made to the DD-patents 209 378, 205 600, 147 039, 146 237 and 138 731, as well as to WO/PCT/93/00008, which show the use of long-chain alcohols, if necessary in combination with propham and/or chloropropham. DD-PS 209 378 also shows medium-chain alcohols of $C_8$-$C_{14}$; DD-PS 205 600 shows the addition of m-chloronaphthalene, and DD-PS 138 731 shows a combination of higher alcohols with the main components nonanol and decanol, where WO 93/00008 shows aromatic aldehydes or alcohols or thymol or mixtures thereof. EP 0 287 946 A2 describes the use of an ethereal oil from a mentha type, in particular oils of *Mentha piperiga L*, as well as peppermint oil and oils of different types of mint.

The drawback of all said sprout inhibitors is that they only supply rather moderate results in spite of the use of relatively large amounts, and, with the exception of the ethereal oils, their utilization for the preservation of foods is actually undesirable because they are not derived from natural products.

As mentioned above, the exclusive use of ethereal oils is prohibitive for practical reasons because the amounts required even when the potatoes are stored without oxygen generally come to 10 to 20 ml oil per 50 kg potatoes with a storage duration of 50 days, and to about twice said amount with a storage duration of 100 days and longer, provided the storage conditions lead to only minor loss of the oils, and that the potatoes are stored at +3° to +8° C.

When using the alcohols and the other agents specified above, the problem of distribution arises, and with a mixture comprising, for example $C_{21}$-$C_{23}$-alcohols with a component of 0.25 to 0.50 mass-% isopropylphenyl carbamate used with a concentration of 200 g active substance per ton of potatoes to be treated, a rather good result was obtained with aggravated storage at 21° C. over three weeks, starting with an addition of 0.5% isopropylphenyl carbamate; however, as previously mentioned, the use of this herbicidal substance is extremely undesirable because there is not assurance that none of this substance penetrates through the potato peel into the potato itself.

It has been found that the use of rape oil methylester as carrier for alcohols, namely all alcohols known from the state of the art and used for this purpose, and also with the ethereal oils known from the state of the art, or mixtures of alcohols with said ethereal oils supplies very good results with respect to sprout inhibition and inhibition of the start of rot with the potatoes, and that rape oil methylester itself, without addition, leads to very good results with respect to sprout inhibition, and to exceptionally good results with respect to rot inhibition.

Of course, this also applies if rape oil methylester is used as carrier for propham or chloropropham, hence isopropylphenyl carbamate or its derivative, which, however, causes certain concerns in terms of food technology, as mentioned a number of times.

Accordingly, the present invention lies in the utilization of rape oil methylester as a sprout inhibitor, if need be in mixture with the known medium- and long-chain alcohols and/or ethereal oils and/or the known chemical sprout-inhibiting agents, whereby combinations of rape oil methylester, alcohol and, if need be, one of the aforementioned ethereal oils, in particular peppermint oil, are preferred in order to achieve the best results. However, rape oil methylester itself is sufficient for technical storage purposes over intermediate time periods with cooling to 6° to 8° C.

The term "medium- and long-chain" alcohols means $C_8$ to >$C_{36}$ alcohols, in particular $C_8$ to $C_{14}$ and $C_{17}$ to $C_{24}$ alcohols, as well as $C_{18}$ to $C_{36}$ alcohols with a component of >$C_{36}$-alcohols, as they are commercially available as Espum EGA 162, now Dehysan®. Espum (Dehysan) has not yet been used for sprout inhibition, so that its use alone or in the claimed mixtures is the object of the present invention as well. Particularly, if used alone or as the predominant part of the composition it is preferably used as an aqueous emulsion i.e., containing 15–40% by weight Espum (Dehysan) preferably 20–30% by weight. Well known, commercially available emulsifiers may be used in a suitable amount.

The term "rape oil methylester" relates to the esterified fatty acids of the rape oil, which are collected upon saponification of the rape oil. This is a commercial product that is relatively inexpensive and readily available.

The term "rape oil" not only relates to rape oil with a rather high content of erucic acid, but includes the oil of the varieties of rape grown at the present time, the so-called double-zero rape varieties, where both the erucic acid and the glycosinolate contents are <1%, and which have only about 0.5% instead of about 48% erucic acid; about 63% as compared to 15% oleic acid; and about 20% linoleic acid instead of 13.5%. However, it comprises about the same percentages of linolenic acid, eicosenic acid, palmitic acid, hexadeceic acid and docosadienic acid.

Rape oil methylesters, particularly those of the double-zero varieties grown now, are safe in terms of health, and, when used as sprout inhibitors or as the basis of the sprout inhibitors, do not damage the potatoes. Additionally, no relevant change occur, for example, in the nitrate content, in the content of reduced sugars and disaccharides, and in the other properties relevant to potatoes. The potatoes treated with said oils, showed in the sensorial test conducted after 19 weeks of storage, typical potato flavor, no foreign flavor, or foreign odor, and exhibited good, solid appearance without any noticeable changes in color.

Rape oil methylester can be easily sprayed such as by a liquid atomization (in particular swingfog) with or without the addition of known sprout-inhibiting agents, including the chemical ones. The spray mist deposits on and between the potatoes with greater layer thickness and exhibits an adequate effect in the mass of the stored potato. It may however also be used in the form of an aqueous emulsion, using well known commerical emulsifiers in a suitable amount.

The amount of rape oil methylester, long-chain alcohols, or combinations thereof lone, or in combination with other active ingredients, which is applied comes to about 50 ml to 100 ml/ton, which is very little, considering the fact that the commercial formulas, which consist of higher alcohols and propham with silicic acid filler, dinitrosopentamethylene tetramine, PVC-powder and kaolin, are used in an amount of about 220 g/ton, and about 40 g/ton is used when chloropropham is utilized alone. Contrast this to ethereal oils which are used in an amount of about 50 ml/50 kg with a storage duration of 100 days and more, an amount of standard time in the industry.

Four (4) lots of 40 kg potatoes each of the Christa variety were treated with compositions based on rape oil methylester with a solidification point of −5° C. and higher alcohols (Espum EGA 162) substantially consisting of 70% $C_{18}C_{36}$ and 30% $>C_{36}$ with a solidification point of +5° C., and in one case with a component of peppermint oil. A blind test was carried out at the same time without any addition.

The composition of the sprout inhibitor used in the specified amount was as follows:

TABLE I

| Test | Alcohol Component (%) | Oil Component (%) | Peppermint Component (%) | Amount used ml/ton | Active Substance ml/ton |
|---|---|---|---|---|---|
| 1 | 30 | 70 | — | 50 | 15 |
| 2 | 40 | 60 | — | 50 | 20 |
| 3 | 25 | 70 | 5 | 50 | 15 |
| 4 | 0 | 0 | 0 | 0 | 0 |

In the present case, the term "active substance" means alcohol+peppermint, thus the component used in addition to rape oil methylester.

The potatoes were stored for 19 weeks at 6° to 8° C. and subsequently examined. The results are summarized in Tables II and III.

TABLE II

EVALUATION OF SPROUT INHIBITION TEST OF THE EXAMPLE

Potato variety: Christa    Duration of storage: 19 weeks

| | Weight of Sample in g | | | | (Start = 100) Weight loss in % | | | Starch Content in % | Share of rot in wt-% | |
|---|---|---|---|---|---|---|---|---|---|---|
| Sample | Start of Storage | End of Storage | Sprouts | Tubers or Sprouts | Tubers or Sprouts | Sprouts | Tubers + Sprouts | Start End of Storage | (tubers or sprouts = 100) | Rot in g |
| 1 | 40,000 | 38,000 | 0.005 | 37,995 | 5.00 | 0.01 | 5.01 | 10.3 | 0.28 | 0.106 |
| 2 | 40,000 | 37,700 | 0.028 | 37,672 | 5.75 | 0.07 | 5.82 | 10.6 | 0.42 | 0.159 |
| 3 | 40,000 | 37,850 | 0.004 | 37,846 | 5.37 | 0.01 | 5.38 | 10.6 | 0.02 | 0.008 |
| 4 | 40,000 | 36,400 | 2.236 | 34,164 | 9.00 | 5.59 | 14.59 | 11.0 | 0.66 | 0.277 |

The following examples are to further illustrate the present invention, but are not meant to be limiting the invention in any way, the meets and bounds of which are set forth in the claims:

EXAMPLE 1

The rape oil or the preparation based on rape oil was distributed over and onto the stored potatoes by liquid atomization (swingfog).

The following four sprout inhibition tests were initially scheduled:

The sensorial test of these fresh potatoes from the sprout inhibition test led to the following result. The potatoes of the Christa variety were tasted after a storage time of 19 weeks. For sprout inhibition, the samples were treated with the following substances:

Sample 1: Rape methylester mixed with long-chain alcohols at a ratio of 70:30
Sample 2: Rape methylester mixed with long-chain alcohols at a ratio of 60:40
Sample 3: Rape methylester mixed with long-chain alcohols and peppermint oil at a ratio of 70:25:5
Sample 4: without any sprout-inhibiting agent=standard

TABLE III

Evaluation

| Sample | Color | Appearance | Odor | Flavor | Consistence |
|---|---|---|---|---|---|
| 1 | Strong yellow with gray tinge | Solid potato | No foreign odor (5×) | No foreign flavor (4×), slightly spicy (1×) | Typical |
| 2 | Strong yellow with gray tinge | Solid potato | No foreign odor (5×), slightly more earthy than sample 1 (1×) | No foreign flavor (5×), slightly more earthy than sample 1 (1×) | Typical |
| 3 | Strong yellow with gray tinge | Solid potato | No foreign odor (5×) | No foreign flavor (4×), slightly spicy (1×) | Typical |
| 4 | Brighter yellow than samples 1, 2 and 3; gray tinge | Wrinkled potato | No foreign odor (5×), slightly stale-smelling (3×) | No foreign flavor (5×), slightly stale (3×) | Slightly more watery than samples 1, 2 and 3 immediately after peeling |

The samples of tests 1, 2 and 3 did not show any significant sensorial differences compared to the untreated fresh potatoes. The potatoes of test 4 did not show any foreign flavor; however, they wrinkled during storage and were slightly more watery immediately after peeling.

Consequently the conditions were substantially the same as in the comparative test according to example 1.

The composition of the sprout inhibitor and the quantities used were as shown on table 4.

| | SPROUT INHIBITION TEST | | | | | | |
|---|---|---|---|---|---|---|---|
| | | Date | | Components in % | | | Quantity used | Active substance |
| Test | Treatment | Storage | Alcohol | Oil | Peppermints | ml/ton | ml/ton |
| 1 | 4/6/93 | 4/27/93 | — | 100 | — | 50 | — |
| 2 | 4/27/93 | 4/29/93 | 30 | 70 | — | 50 | 15 |
| 3 | 5/3/93 | 5/5/93 | 40 | 60 | — | 50 | 20 |
| 4 | 5/5/93 | 5/7/93 | 25 | 70 | 5 | 50 | 15 |
| 5 | 5/7/93 | 5/10/93 | 50 | 50 | — | 50 | 26 |
| 6 | Control | | | | | | |

Sample size: 4 × 20 kg
Quantity used: 4 ml
Air circulation time: 20 min
After-storage: 48 h
Storage: basement, each test quantity stored on separate pallet

EXAMPLE 2

This example shows the use of rape oil methyl ester alone and in combination with alcohol and pepper mint oil.

The potatoes, which were used in each of tests 1 to 5 in an amount of 40 kg, and in an amount of 20 kg in comparative test 6, were stored over 9 weeks at 6° to 8° C.

Only rape oil methylester was used in test 1, and in tests 2 and 3 as well as 5 treatment was carried out with a mixture of rape oil methylester with a solidification point of −5° C. and higher alcohols (Espum EGA 162) substantially consisting of 70% $C_{18}$-$C_{36}$ and 30% >$C_{36}$ with a solidification point of +5° C., and in test 4 with a component of peppermint oil. No treatment was carried out in test 6 "control".

In this test too, the term "active substance" means alcohol+ peppermint oil and, therefore, is the component used in addition rape oil methylester.

The potatoes were stored for 66 days at 6° to 8° C. and were then examined. The results are summarized in the following table 5:

| | EVALUATION OF SPROUT INHIBITION TEST | | | | | | | |
|---|---|---|---|---|---|---|---|---|
| | Weight of sample in g | | | | Weight loss in % | | | Share of rot |
| Test | Start of storage | End of storage | Sprouts | Tubers or sprouts | Tubers or sprouts | Sprouts | Tubers + sprouts | (tubers or sprouts = 100) | Rot in g |
| 1 | 40,000 | 37,700 | 237 | 37,463 | 5.75 | 0.59 | 6.34 | 1.02 | 382 w + d |
| 2 | 40,000 | 37,250 | 299 | 36,951 | 6.87 | 0.75 | 7.62 | 2.44 | 899 w + d |
| 3 | 40,000 | 37,550 | 493 | 37,057 | 6.12 | 1.23 | 7.35 | 1.03 | 376 d |
| 4 | 40,000 | 37,450 | 480 | 36,970 | 6.37 | 1.20 | 7.57 | — | — |
| 5 | 40,000 | 37,500 | 613 | 36,887 | 6.25 | 1.53 | 7.78 | 0.60 | 221 w |
| 6 | 20,000 | 17,900 | 1,855 | 16,045 | 10.50 | 9.27 | 19.77 | — | — |

Storage days: 66
n = wet rot
t = dry rot

The share of rot in test 4 and also with comparative test 6 (untreated control) was practically zero. However, sprout inhibition was very good with test 4, and very poor with control test 6.

EXAMPLE 3

In a further test the long-chain alcohol Espum EGA 162, now marketed as Dehysan was used alone and compared with rape oil methylester alone and peppermint oil. The effectiveness of the alcohol (Espum, now Dehysan) is about the same as that of the rape oil methylester alone. Addition of 5% by weight of peppermint oil in both cases, that is 95% by weight alcohol or rape oil methylester plus 5% by weight peppermint oil clearly gives a still better result.

The amount used was 50 ml/t in each case.

Due to the high viscosity of the long-chain alcohol it was difficult to atomize it sufficiently. Thus, in another experiment the alcohol was used as an aqueous emulsion containing 25% by weight of the alcohol with a commerically available fatty alcohol polyglycol ether sulfate as an emulsifier in an amount of about 1 g/l emulsion.

The results were somewhat better than using the non-emulsified alcohol as such.

We claim:

1. A sprout inhibitor which comprises at least 60% by weight rape oil methylester and up to 40% by weight of a further component selected from the group consisting of medium-chain alcohols, long-chain alcohols, and combinations thereof.

2. A sprout inhibitor according to claim 1, which comprises rape oil methylester, up to about 10% by weight ethereal oil, and from 0.1 to 1% by weight of a known chemical sprout-inhibiting agent selected from the group consisting of medium-chain alcohols, long chain alcohols, propham, chloropropham, isopropylphenyl carbamate, m-chloronapthalene, aromatic aldehydes, thymol or combinations thereof.

3. A sprout inhibitor of claim 2 wherein the ethereal oil is peppermint oil.

4. A sprout inhibitor of claim 2, wherein the chemical sprout-inhibiting agent is selected from the group consisting of propham, chloropropham and combinations thereof.

5. A sprout inhibitor according to claim 1, wherein the sprout inhibitor comprises at least 70% by weight, rape oil methylester.

6. The process of inhibiting sprouting of potatoes comprising applying to potatoes the sprout inhibitor of claim 1 in amounts of 50 to 100 ml sprout inhibitor per ton of potatoes, prior to storage of the potatoes.

7. The process of claim 6 whereby the sprout inhibitor is applied by means of liquid atomization.

8. The process of inhibiting sprouting of potatoes comprising applying a sprout inhibitor comprising about 70% $C_{18}$-$C_{36}$ and 30%>$C_{36}$ long-chain alcohols alone or in a mixture according to claim 1 in amounts of 50 to 100 ml sprout inhibitor per ton of potatoes.

9. The process of claim 8 wherein the long-chain alcohols form an aqueous emulsion, said emulsion comprising about 15–40% by weight of the long-chain alcohols, and 5% by weight, alcohols of ethereal oil.

10. A process of inhibiting sprouting of potatoes comprising applying to the potatoes a sprout inhibitor comprising rape oil methylester in amounts of 50 to 100 ml sprout inhibitor per ton of potatoes, prior to storage of the potatoes.

11. The process of claim 10 wherein the sprout inhibitor is applied by means of liquid atomization.

* * * * *